United States Patent [19]
Ohnishi et al.

[11] Patent Number: 4,591,504
[45] Date of Patent: May 27, 1986

[54] HUMAN LEUCOCYTE PEPSIN-LIKE ENZYME AS A THERAPEUTIC AGENT FOR TREATING ALLERGIC DISORDERS AND IMMUNE COMPLEX DISEASES

[75] Inventors: Haruo Ohnishi, Funabashi; Hiroshi Kosuzume, Yokohama; Yasuo Suzuki, Kawaguchi; Ei Mochida, Tokyo, all of Japan

[73] Assignee: Mochida Pharmaceutical Co., Ltd., Tokyo, Japan

[21] Appl. No.: 498,506

[22] Filed: May 26, 1983

[30] Foreign Application Priority Data

May 31, 1982 [WO] PCT Int'l Appl. ... PCT/JP82/00213

[51] Int. Cl.$^4$ .......................... A61K 37/48; C12N 9/48
[52] U.S. Cl. ...................................... 424/94; 424/101; 435/212; 435/219; 435/226
[58] Field of Search .................. 424/94, 101; 435/212, 435/219, 226

[56] References Cited

U.S. PATENT DOCUMENTS 3,796,636  3/1974  Gallagher et al. .................. 435/226
4,229,540 10/1980  Coan .................................. 435/219

OTHER PUBLICATIONS

Mirsky et al., Source, Properties and Assay of Uropepsin, "Uropepsin Excretion by Man", pp. 818–839.

Primary Examiner—Sam Rosen
Attorney, Agent, or Firm—Parkhurst & Oliff

[57] ABSTRACT

This invention provides a human leucocyte pepsin-like enzyme and a therapeutic agent and method for treating allergic disorders, immune complex diseases and tumors, the agent containing the enzyme as an effective ingredient. The human leucocyte pepsin-like enzyme of this invention is a protein of human origin and, therefore, a therapeutic agent containing said enzyme as an effective ingredient shows extremely little adverse reactions such as anaphylaxis and thus is highly safe.

11 Claims, 4 Drawing Figures

HUMAN LEUCOCYTE PEPSIN-LIKE ENZYME AS A THERAPEUTIC AGENT FOR TREATING ALLERGIC DISORDERS AND IMMUNE COMPLEX DISEASES

TECHNICAL FIELD

This invention relates to a human leucocyte pepsin-like enzyme, method for preparation of the enzyme, and method and a therapeutic agent for treating allergic disorders, immune complex diseases and tumors, said agent containing said enzyme as an effective ingredient.

BACKGROUND ART

Allergic disorders are caused by an allergic reaction which, as a result of an antigen-antibody reaction, brings about a pathogenesis in a living organism. The mechanism of pathogenesis of allergic disorders is believed to follow the following course. When exposed to a pathogenic antigen, a living organism produces antibodies. The second attack of the same antigen causes an antigen-antibody reaction and, as a result, chemical mediators are released from the cells. These mediators damage tissues and/or the formed antigen-antibody complexes are deposited on the tissues, causing allergic disorders or autoimmune disorders. Among various pathogenic antigens are included xenogenic antigens, such as inhaled allergen, food allergen, drugs, contact allergen, and allogenic or autolous antigens which originate from autologus components of the tissues or organs denatured for some reason and thereby behaving as foreign substances.

So-called allergic disorders caused by enogenic antigens, such as bronchial asthma, food allergy or urticaria, are classified into four types according to their symptoms or causes. That is, they are classified into Type I allergies (anaphylactic-type) resulting from tissue-depositing antibodies and characterized by increased capillary permeability and smooth muscle contraction, Type II allergies (cytotoxic-type) resulting in the presence of complements and characterized by cell damage, Type III allergies (Arthus-type) resulting from the deposition of antigen-body complexes on vacular walls and subsequent participation of complements and polymorphonuclear leucocytes and characterized by inflammatory reactions, and Type IV allergies resulting from cell-mediated immunity and characterized by the appearance of delayed hypersensitivitiy such as Tuberculin reaction. Among the allergic reactions, Types I, III and IV allergies participate in, for example, bronchial asthma and each of these reactions is considered independently or in combination to cause asthma attack. The pathogenic mechanism of these allergic disorders can be considered to act as follows.

An antigen which invades a living organism is treated by macrophages, and the immunological information on the antigen is transmitted to the T cell-B cell system. The B cells which have received the information produce immunoglobulin (Ig E antibody is mainly produced in Type I allergies and Ig G antibody is mainly produced in Type II and Type III allergies) and the Ig E antibody binds to the basophils in the circulation or to the most cells in the tissues, thereby establishing the state of sensitization. The same antigens which invade the sensitized organism bind to cell-bound antibodies, allowing them to release chemical mediators such as histamine and slow-reacting substances of anaphylaxis (SRS-A). The released chemical mediators induce allergic symptoms such as erythema, edema or increase of glandular secretion caused by contraction of smooth muscles and increase of capillary permeability. On the other hand, Ig G antibody binds to polymorphonuclear leucocytes to achieve sensitization and the subsequent secretion of SRS-A as a chemical mediator is also suspected.

Anti-allergic agents may achieve therapeutic purpose by suppressing any step in these processes.

Conventionally, xanthine derivatives, β-adrenergic stimulants (β-stimulants) or corticosteroids have been used for the treatment of asthma. However, these drugs are frequently observed to show undesirable adverse reactions. For instance, palpitation, tachycardia, etc., are reported with respect to xanthine derivatives and β-stimulants. Furthermore, corticosteroids cause adverse reactions such as peptic ulcers and complications of bacterial infection. Moreover, anti-histamine agents may cause difficulty in the expectoration of tracheal secretion, rather than being effective against asthma attack, so that they may sometimes worsen the clinical condition of asthma.

Immune complex diseases or autoimmune disorders in which the pathogenic antibody is an auto-antigen, typified by rheumatoid arthritis, systemic lupus erythematosus (SLE) and lupus nephritis, as implied by the names, are disorders resulting from complexes of antigens and antibodies, namely, immune complexes. Although the pathogenetic mechanism of immune complex diseases is complicated and has not been resolved in many respects, it is generally believed to follow the following course. When the tissues are damaged by bacterial or viral infections, antibodies are produced against the freshly produced autoantigens or virally-infected cells and they react with the corresponding antigens to form immune complexes. Since these immune complexes activate the complement system and platelets, vasoactive substances such as histamine and serotonin are released and the permeability of the blood vessels is increased. Then, the immune complexes in circulation penetrate into the vascular walls having increased permeability and deposit along the basement membranes. Polymorphonuclear leucocytees are gathered on the deposited sites of the immune complexes by the action of the leucocyte chemotactic factors produced by the addition of the complement upon the deposited immune complexes. The polymorphonuclear leucocytes, reacting with the immune complexes, release various tissue-damaging substances such as cathepsin D and E, collagenase, elastase and permeability factors, and these substances eventually damage the tissue. The level of complement in the serum from a patient with an immune complex disease such as SLE is generally low and aggravation of the disease conditions is closely correlated with the decrease of the complement level. This decline of complement level is considered to be due to a plentiful consumption of complement at the site of the reaction between antigens and antibodies taking place such as kidneys and blood vessels. Moreover, it is considered that the immune complexes are also related to blood coagulation systems and they are believed to lead to more serious conditions through diverse mechanisms such as the acceleration of fibrinoid deposition onto the damaged tissues.

For the treatment of immune complex diseases, anti-inflammatory agents and immunosuppressive agents including steroids are presently used for suppressing the hypersensitized immune system and for reducing local inflammations and pains, or anticoagulants and antiplatelet agents are used for improving abnormalities of the coagulation-fibrinolysis system in the blood vessels. However, because these drugs show eak effectiveness and are associated with strong adverse reactions, it has been strongly desired to develop drugs which are safe and highly effective in the treatment of the diseases.

Furthermore, many drugs have been developed for the treatment of malignant tumors. These anti-tumor drugs are roughly classified into the following two types. The first type includes so-called cytotoxins which directly suppress tumor growth. The second type includes those drugs which indirectly control the growth of tumors by recognizing them as foreign substances through the activation of immunological protective functions of the host. However, drugs belonging to the former type do not have sufficient selective toxicity to tumor cells, and are toxic against normal cells of the host as well. Accordingly, their total dosage is limited considerably. On the other hand, the latter type, i.e. immunopotentiators, show unfavorable adverse reactions less frequently as compared with the former so that they are generally safely used. However, they have an essential problem in that since a tumor in itself is originated from normal cells of a patient any may not be sufficiently recognized as a foreign substance by the immunological protective functions, some immunopotentiators do not exhibit sufficient anti-tumor effect.

SUMMARY OF THE INVENTION

An object of this invention is to provide a human leucocyte pepsin-like enzyme having an anti-allergic disorder, anti-immune complex disease and anti-tumor activity.

Another object of this invention is to provide processes for producing a human leucocyte pepsin-like enzyme.

A further object of this invention is to provide a therapeutic agent for allergic disorders, immune complex diseases and tumors which contains a human leucocyte pepsin-like enzyme as an active ingredient.

A still further object of this invention is to provide a method for treating allergic disorders, immune complex diseases and tumors by administering a human leucocyte pepsin-like enzyme.

DETAILED DESCRIPTION OF THE INVENTION

As a result of an intensive investigation for a long period to develop a more effective therapeutic agent against allergic disorders, immune complex diseases and tumors, the inventors of this invention have found that a pepsin-like enzyme present in human leucocytes (hereinafter referred to as a human leucocyte pepsin-like enzyme) has a strong anti-allergic effect and a remarkable suppressive effect against various immune complex diseases, and at the samt time shows an excellent anti-tumor effect. The present invention has been accomplished based upon the above findings.

The human leucocyte pepsin-like enzyme exists not only in human leucocytes but also in cells such as promyelocytic leukemic cells strain HL-60 treated with a substance for inducing differentiation such as actinomycin D and can be obtained from a supernatant liquid of a homogenate of these cells by an appropriate combination of ordinary methods used in purification of proteins, for example, salting-out, adsorption chromatography on an inorganic adsorbent, ion-exchange chromatography on an ion-exchange resin and gel chromatography with a molecular sieve effect. Furthermore, the enzyme can be obtained in large quantities from cultured cells prepared by fusing tumor cells with pepsin-like enzyme-producing cells such as human leucocytes or by a genetic engineering technique, for example, by preparing complementary DNA with the aid of a reverse transcriptase by using as a template the messenger RNA for human leucocyte pepsin-like enzyme and thereafter integrating this DNA into E. coli to produce the enzyme.

The pharmacological action and toxicity of this human leucocyte pepsin-like enzyme will now be described with reference to experimental examples.

EXPERIMENTAL EXAMPLE 1

Suppressive effect on production of anti-ovalbumin Ig E antibody

Figure 1:
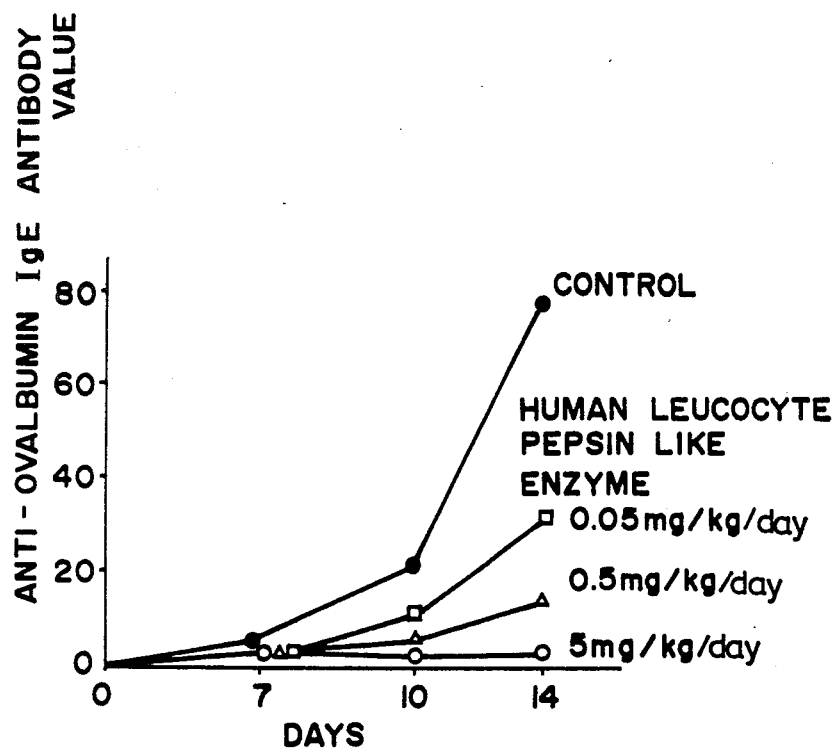
FIG. 1 is a graph showing the results of Experimental Example 1.

Groups each consisting of 10 Wistar strain male rats each weighing 180 to 200 g were used. One-tenth mg of ovalbumin together with 20 mg of aluminum hydroxide gel was injected intraperitoneally. From the next day on, the human leucocyte pepsin-like enzyme was injected intravenously once a day for 14 days. After 7, 10 and 14 days from the administration of ovalbumin, blood samples were taken and measured for the level of anti-ovalbumin Ig E antibody in the serum by the homologous PCA rat reaction (H. Maruyama, et al., Folia Pharmacologica Japonica, 74, 179, 1978). The results are shown in FIG. 1.

Production of anti-ovalbumin Ig E antibody was significantly suppresed by administration of the human leucocyte pepsin-like enzyme.

EXPERIMENTAL EXAMPLE 2

Suppressive effect on bronchial asthma

Groups each consisting of 10 Wistar strain male rats each weighing 180 to 200 g were used. One-tenth mg of ovalbumin together with 20 mg of aluminum hydroxide gel was injected intraperitoneally and, from the next day forward, the human leucocyte pepsin-like enzyme was injected intravenously once a day for 14 days. After 14 days, 25 mg/kg of ovalbumin was administered intravenously to induce bronchial asthma, and the resulting tracheal contraction was measured according to the method of Konzett and Rössler (Arch. Exptl. Path. Pharmacol. 195, 71, 1940). The relative contraction rate of the trachea of each group was calculated when the contraction of the control group was taken as 100. The results are shown in Table 1.

TABLE 1

| | Dose | Contraction rate of trachea (%) |
|---|---|---|
| Control | | 100 |
| Human leucocyte pepsin-like enzyme | 0.05 mg/kg | 73 |
| | 0.5 mg/kg | 49 |
| | 5 mg/kg | 23 |

The tracheal contraction was suppressed significantly by the administration of the human leucocyte pepsin-like enzyme.

EXPERIMENTAL EXAMPLE 3

Suppressive effect on Masugi nephritis

Figure 2:
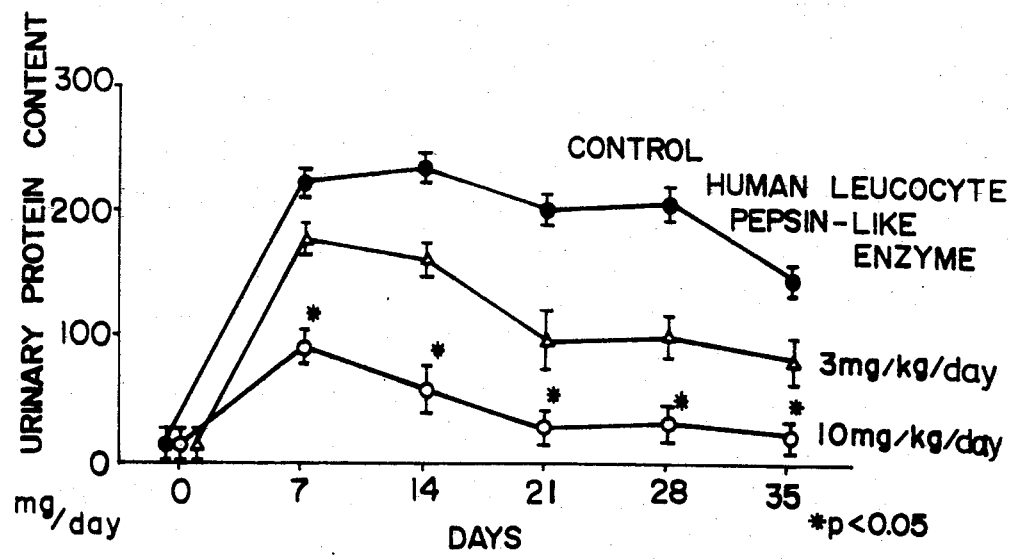
FIG. 2 and FIG. 3 are graphs showing the results of Experimental Example 3.
Figure 3:
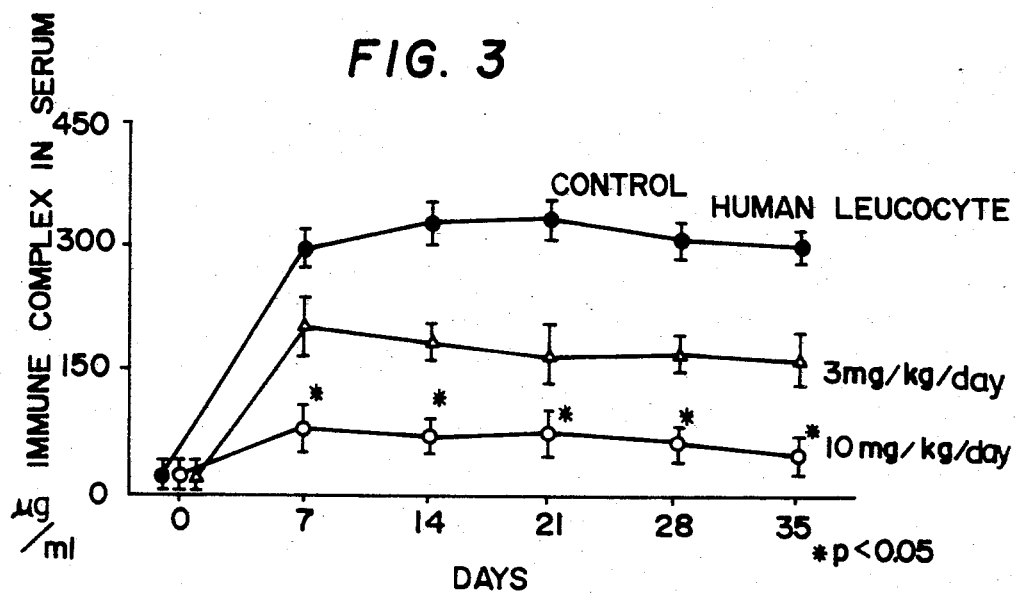

According to the method of Suzuki et al. (Folia Pharmacologica Japonica, 68, 572, 1972), rabbit anti-rat kidney serum was administered intravenously to groups each consisting of 10 Wistar strain male rats at a dose of 5 ml/kg to induce nephritis. After the occurence of nephritis, blood and urine samples were taken at regular intervals to measure the levels of serum immune complex and urinary protein. The human leucocyte pepsin-like enzyme was injected intravenously once a day after the administration of the anti-rat kidney antibody, and the control group was similarly administered inactivated human leucocyte pepsin-like enzyme. The results are shown in FIGS. 2 and 3.

In the groups treated with the human leucocyte pepsin-like enzyme, decreases in urinary protein and blood immune complex were observed.

EXPERIMENTAL EXAMPLE 4

Suppressive effect on spontaneous kidney disorder

Measurement was made according to the method of Abe et al. (The Ryumachi, 14, 43, 1974).

Figure 4:
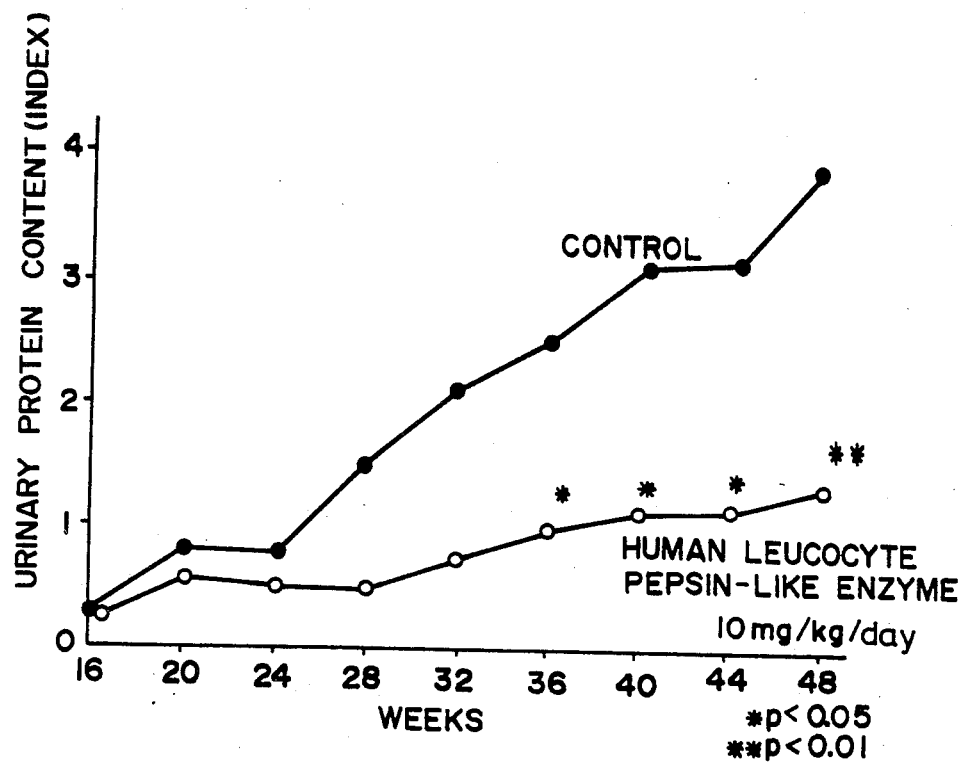
FIG. 4 is a graph showing the results of the measurement of urinary protein in Experimental Example 4, wherein the content of urinary protein was measured on the basis of the coloration of the test paper and expressed in terms of an average of indices of a group. This index system consists of the numerals 0, 1, 2, 3 and 4, respectively corresponding to the colorations of (−), (+), (++), (+++) and (++++).

Groups each consisting of sixteen 16-week old female mice (NZB×NZW) $F_1$, were injected with the human leucocyte pepsin-like enzyme intravenously at a dose of 10 mg/kg once a day. A control group was similarly administered inactivated human leucocyte pepsin-like enzyme intravenously. Every fourth week, the urinary protein of the mice was measured by a commercial test paper (Combisticks). The results are shown in FIG. 4. Furthermore, 6 mice from each group were sacrificed at the age of 32 weeks and the cell infiltration into renal glomeruli was observed. The remaining 10 mice of each group received continued daily administration, and the survival rate at the age of 50 weeks was determined. The results are shown in Table 2.

It was observed that by administration of the human leucocyte pepsin-like enzyme, the increase of urinary protein was significantly suppressed, cell infiltration after 32 weeks was slight and the survival rate at 50 weeks was higher in the groups treated with the human leucocyte pepsin-like enzyme. These results indicate that the spontaneous kidney disorders in mice were suppressed by the human leucocyte pepsin-like enzyme.

TABLE 2

| | Control group | Group treated with the human leucocyte pepsin-like enzyme |
|---|---|---|
| Cell infiltration | heavy infiltration in microlymphocytes and plasmocytes | slight infiltration around vessel wall |
| Survival rate | 20% | 80%* |

*$p < 0.05$

EXPERIMENTAL EXAMPLE 5

Suppressive effect on thyroiditis

This experiment was carried out according to the method of Kotani et al. (Clinical Immunology, 9, (8), 635, 1977). Groups each consisting of 10 BUF/HDK male rats (6 weeks old) were subjected to thymectomy and thereafter they were exposed to X-ray irradiations each of 200 rads and repeated four times at an interval of two weeks. After 14 weeks from the thymectomy, the rats were sacrificed to exsaguinate. The thyroid glands were isolated and embedded in a paraffin block and then stained with hematoxylin-eosin or with azan. The severity of the throiditis was estimated according to the grades of 0 to 4 on the basis of infiltration of mononuclear cells, destruction of endoplasmic reticulum and glandular fibrosis. The human leucocyte pepsin-like enzyme was administered to the animals intravenously once a day, and the control group was similarly administered inactivated human leucocyte pepsin-like enzyme. The results are shown in Table 3.

As compared with the control group, in the groups treated with the human leucocyte pepsin-like enzyme, both the occurrence and the severity of thyroiditis were decreased in a dose dependent manner.

TABLE 3

| | Occurrence (%) | Severity |
|---|---|---|
| Control | 90 | 3.5 ± 0.4 |
| Human leucocyte pepsin-like enzyme | | |
| 1 mg/kg | 80 | 3.0 ± 0.5 |
| 3 mg/kg | 60 | 1.9 ± 0.2* |
| 10 mg/kg | 40* | 1.3 ± 0.1** |

*$p < 0.05$
**$p < 0.01$

EXPERIMENTAL EXAMPLE 6

Hydrolysis of human immune complex

Serum was obtained from patients with rheumatoid arthritis, systemic lupus erythematosus and hepatitis who had been proved to carry immune complex in their serum. The human leucocyte pepsin-like enzyme was added to 1 ml of the serum in an amount of 10, 30 or 100 μg, and the serum was incubated at 37° C. for 60 minutes. After the reaction, the amount of immune complex in the serum was measured by the hemolytic reaction of sheep erythrocytes in the presence of guinea pig complement according to the method of Fust et al. (Atherosclerosis, 29, 181, 1978) wherein aggregated human Ig G was used as a standard substance. The results are shown in Table 4.

TABLE 4

| Diseases | Serum No. | Amount of human leucocyte pepsin-like enzyme added (μg/ml) | Immune complex content (μg/ml) |
|---|---|---|---|
| Rheumatoid arthritis | 1 | 0 | 78 |
| | | 10 | 65 |

TABLE 4-continued

| Diseases | Serum No. | Amount of human leucocyte pepsin-like enzyme added (μg/ml) | Immune complex content (μg/ml) |
|---|---|---|---|
| | | 30 | 53 |
| | | 100 | below 50 |
| | 2 | 0 | 234 |
| | | 10 | 180 |
| | | 30 | 150 |
| | | 100 | 123 |
| Systemic lupus erythematosus | 1 | 0 | 420 |
| | | 10 | 352 |
| | | 30 | 211 |
| | | 100 | 124 |
| | 2 | 0 | 125 |
| | | 10 | 70 |
| | | 30 | 56 |
| | | 100 | below 50 |
| Hepatitis | 1 | 0 | 65 |
| | | 10 | 58 |
| | | 30 | below 50 |
| | | 100 | below 50 |
| | 2 | 0 | 70 |
| | | 10 | 66 |
| | | 30 | 55 |
| | | 100 | 51 |

The human leucocyte pepsin-like enzyme reduced the amount of immune complex in the serum of the patients suffering from chronic rheumatism, systemic lupus erythematosus and hepatitis in a dose dependent manner.

EXPERIMENTAL EXAMPLE 7

Effect on the growth of cultured human breat cancer cells MX-1 and mouse leukemia cells L1210

Human breast cancer cells MX-1 and mouse leukemia cells L1210 were respectively suspended at a cell concentration of $10^5$/ml in Eagle's medium containing 10% calf serum and test substances. The cells were cultured at 37° C. under 5% $CO_2$ for 48 hours. Then the number of viable cells was counted after staining with Tripan Blue. The growth inhibition rate was calculated according to the following equation and the results are shown in Table 5.

Growth inhibition rate =

$$\left(1 - \frac{\text{Number of viable cells in treated group}}{\text{Number of viable cells in control group}}\right) \times 100$$

TABLE 5

| | Concentration added (μg/ml) | Growth inhibition rate (%) MX-1 | Growth inhibition rate (%) L1210 |
|---|---|---|---|
| Human leucocyte pepsin-like enzyme | 30 | 16 | 7 |
| | 100 | 32 | 22 |
| | 300 | 55 | 29 |
| Mitomycin C | 100 | 48 | 61 |

The human leucocyte pepsin-like enzyme inhibited the growth of tumor cells even at low concentration.

EXPERIMENTAL EXAMPLE 8

Effect on leukemia cells P388 bearing mice $10^5$ of leukemia cells P388 were transplanted intraperitoneally to a group of 5 $BDF_1$ male mice. The human leucocyte pepsin-like enzyme was injected intravenously into the mice twice a day beginning on the next day until the animals died. The average life span was calculated and expressed as a percentage of control. The results are shown in Table 6.

Average life span (%) =

$$\frac{\text{Mean survival days of treated group}}{\text{Mean survival days of control group}} \times 100$$

TABLE 6

| | Dose (mg/kg) | Average life span (%) |
|---|---|---|
| Control | | 100 ± 5 |
| Human leucocyte pepsin-like enzyme | 0.3 | 109 ± 5 |
| | 1.0 | 120 ± 8 |
| | 3.0 | 124 ± 8* |
| Mitomycin C | 0.5 | 135 ± 16 |

*$p < 0.05$

The human leucocyte pepsin-like enzyme clearly increased average life span.

EXPERIMENTAL EXAMPLE 9

Effect on human brest cancer MX-1 transplanted to a nude mouse

Two mm-square pieces of human breast cancer MX-1, which had been subcultured on nude mice (BALB/C, nu/nu), were transplanted subcutaneously on the backs of animals in groups each consisting of 5 nude mice of the said strain. From two weeks later, the human leucocyte pepsin-like enzyme was administered intravenously twice a day for 18 days. After 18 days from the first administration of the human leucocyte pepsin-like enzyme, the tumors were isolated and weighed. The results are shown in Table 7.

TABLE 7

| | Dose (mg/kg) | Weight of tumor (g) |
|---|---|---|
| Control | | 1.34 ± 0.10 |
| Human leucocyte pepsin-like enzyme | 0.3 | 0.76 ± 0.12* |
| | 3.0 | 0.66 ± 0.13* |

*$p < 0.05$

The human leucocyte pepsin-like enzyme showed a significant anti-tumor effect even at the lower dose.

EXPERIMENTAL EXAMPLE 10

Acute toxicity

Groups each consisting of 10 ddY mice weighing 20±1 g were administered intravenously or intraperitoneally 2 g/kg of the human leucocyte pepsin-like enzyme dissolved in physiological saline solution. Then, the mice were kept under daily observation for any toxicological symptoms for a week. No sign of any toxicity was observed throughout the period.

As described in the above Experimental Examples, the human leucocyte pepsin-like enzyme which is an effective ingredient of the pharmaceutical agent of the present invention clerly suppressed production of Ig E antibody and showed a distinct therapeutic effect against experimental asthma. Moreover, the enzyme clearly suppressed the establishment and development of a number of diseases which are believed to be induced by immune complexes, for example, thyroiditis and nephritis. Still further, this human leucocyte pepsin-like enzyme exhibited a strong anti-tumor effect.

Judging from the results of the acute toxicity study, the dosage required to obtain these effects is within a sufficiently safe range. It is considered that because this human leucocyte pepsin-like enzyme is a protein of human origin, it has little danger of inducing serious adverse reactions due to antigenicity, such as anaphylactic shock. Therefore, it can provide a highly useful therapeutic agent against various allergic disorders such as bronchial asthma, urticaria, hay fever, contact dermatitis, food allergy, drug allergy, allergic rhinitis, hypersensitivity pneumonitis, various immune complex diseases such as systemic lupus erythematosus, glomerulonephritis with immune complex, periarteritis nodosa, rheumatoid arthritis, immune complex hepatitis, thyroiditis, serum sickness, myasthenia gravis, and various tumors such as gastric cancer, lung cancer, colon cancer, breast cancer, prostatic cancer, uterine cancer, bladder cancer, leukemia, esophagal cancer, lymphomas.

BEST MODE FOR CARRYING OUT THE INVENTION

The human leucocyte pepsin-like enzyme can be prepared as follows. The supernatant of human leucocyte homogenate is passed through a DEAE-cellulose column equilibrated with 0.1M acetate buffer solution (pH 5.3) to adsorb the enzyme. The adsorbed enzyme is eluted with the same buffer solution containing 0.5M sodium chloride. The eluate can be concentrated and further purified by gel-chromatography on a column of Sephadex G-100 swollen with 0.9% physiological saline solution. The human leucocyte pepsin-like enzyme is found to possess a molecular weight of 35,000 to 41,000 by gel chromatography on Sephadex G-100; an isoelectric point in the range of pH 2.5 to 3.5 by isoelectrofocusing on Ampholine; a maximum adsorption at 278 nm; shows a positive reaction to ninhydrin; and is readily soluble in water and insoluble in ether and chloroform. Furthermore, the human leucocyte pepsin-like enzyme shows a high hydrolytic activity to hemoglobin in the acidic range of below pH 7.0 and its optimal pH is 2.0 to 3.5.

The agent of the present invention is generally prepared in the form of an injectable solution and is injected intravenously, subcutaneously, intramuscularly or intraarticularly or to the local site of a tumor itself. However, it can also be used in the form of an oral agent, inhalant or rectal suppository. The daily dose of the human leucocyte pepsin-like enzyme is 1 to 1,000 mg, preferably 50 to 500 mg, but it can be suitably increased or decreased depending on age, symptoms and the manner of application.

The human leucocyte pepsin-like enzyme can be formulated to a pharmacological agent by a conventional method together with any conventional pharmaceutical carriers or excipients.

Preparations for injection may include lyophilized preparations which are dissolved at the time of administration and liquid preparations; controlled release preparations are also preferred to keep a prolonged effective concentration.

Oral preparations may be in the form of capsules, tablets, granules, powders or liquid oral preparations; they are preferably in the form of liposome inclusion bodies for the purpose of promoting absorption.

The inhalants are preferably in the form of lyophilized preparations; for rectal administration, the form of suppository is preferred.

Examples of this invention will follow.

EXAMPLE 1

HL-60 leukemia cells ($10^{11}$ cells) previously treated with Actinomycin D were suspended in 1 l. of 0.9% physiological saline solution and then destroyed in a homogenizer. The supernatant liquid obtained by centrifugation (10,000 rpm, 30 min.) was concentrated and desalted by using an ultra-concentrator (Millipore, Diaflow Model-202). The concentrated solution was applied to a DEAE cellulose column (10×50 cm) equilibrated with 0.01M phosphate buffer solution (pH 7.0). The column was washed with 4 l. of the same buffer solution containing 0.1M NaCl and an active fraction was eluted with the same buffer solution containing 0.4M NaCl. Then, the active fraction was applied to a column of Sephadex G-100 (10×90 cm) equilibrated with pyrogenfree 0.9% physiological saline solution and subjected to gel filtration to yield 50 mg of the pepsin-like enzyme. The specific activity of the pepsin-like enzyme was 1930 u/mg when the enzyme activity was measured according to the method of Anson (J. Gen. Physiol. 22, 79, 1938) by using Swine pepsin as a standard substance and denatured hemoglobin as a substrate.

EXAMPLE 2

Human leucocytes ($10^{10}$ cells) were suspended in 20 mM Tris-HCl buffer solution (pH 7.4) containing 1% of Triton X-100, 10 mM of a vanadyl comples, 3 mM of magnesium acetate, 10 mM of NaCl and 5% of sucrose and the cells were destroyed in a Teflon homogenizer. The polysome fraction was collected from the homogenate by centrifugation and m-RNA was extracted with phenol from the polysome fraction followed by precipitation with ethanol. To this precipitate was added 0.2M Tris-HCl buffer solution (pH 9.0) containing 0.5% of SDS, 0.01M of EDTA and 50 mM of NaCl, and the mixture was incubated at 70° C. for 3 minutes. This m-RNA solution was adsorbed on an oligo (dT) cellulose column. The column was washed and then eluted with 10 mM Tris-HCl buffer solution (pH 7.4) containing 0.5% of SDS and 1 mM of EDTA to obtain a fraction of m-RNA containing Poly A. This m-RNA was further fractionated by a sucrose density gradient at a concentration of 5 to 25%. The fractions were monitored for m-RNA activity corresponding to the pepsin-like enzyme in the protein synthesis sytem of the ovocytes of Xenopus, and an active fraction was obtained. Five µg of the pepsin-like enzyme m-RNA thus prepared was added to 100 µl of 40 mM Tris-HCl buffer solution (pH 7.5) containing 1 µg of oligo $(dT)_{10}$, 5 mM of mercaptoethanol, 0.5 mM of dATP, dTTP, dGTP and dCTP and 10 units of reverse transcriptase (AMV-RT) and incubated at 42° C. for 90 minutes. After the incubation period, RNA was removed by deproteination and an alkali treatment to obtain complementary DNA. This DNA was then incubated in the same medium as used in the preparation of the above complementary DNA (provided that oligo $(dT)_{10}$ was not contained) to obtain a double-stranded complementary DNA. After treatment with 0.25 unit of nuclease SI, the double-stranded complementary DNA was added to 30 µl of 140 mM cacodylic acid solution (pH 7.6) containing 5 units of terminal transferase, 1 mM of dATP, 0.1 mM of dithiothreitol, 30 mM of trihydroxylamine and 1 mM of cobalt chloride and incubated at 37° C. for 15 minutes to effect the addition of deoxyandenine chains.

On the other hand, 3 μg of *E. coli* plasmid pBR 322 DNA was treated with 0.25 unit of EcoRI at 37° C. for 20 hours and further incubated together with 17.5 units of an exonuclease at 0° C. for 90 minutes. After the incubation, deoxythymidine chain plasmid DNA was obtained in the similar manner as in the preparation of the above deoxyadenine chain DNA (provided that dTTP was used instead of dATP).

The deoxythymidine chain plasmid DNA thus produced and the above deoxyadenine chain DNA were associated by treatment at 65° C. for 2 minutes, 46° C. for 120 minutes, 37° C. for 60 minutes and 23° C. for 60 minutes in 50 mM Tris-HCl buffer solution (pH 7.5) containing 5 mM of EDTA and 0.1M of NaCl.

Then, *E. coli* NIHJ C-2 were transformed by using the recombined plasmid DNA and cloned from ampicillin-resistant strain 5000. The cloned DNA was introduced into *E. coli* by connecting to the promotor site of the tryptophan operon according to the method of Goeddel et al. (Nature, 287,411, 1980). A strain (E-931) which showed the production of the pepsin-like enzyme at high concentrations was cultured in LB medium containing 20 mg/l of ampicillin. From the supernatant liquid obtained from the homogenate of 17 kg of the cultured cells, 3.5 g of the pepsin-like enzyme was obtained in the same manner as in Example 1.

EXAMPLE 3

One g of human leucocyte pepsin-like enzyme was dissolved in 100 ml of physiological saline solution and filtered aseptically through a membrane filter. One milliliter portions of the filtrate were placed in sterilized glass vessels and sealed after lyophilization to obtain lyophilized powder preparations.

EXAMPLE 4

One g of the lyophilized human leucocyte pepsin-like enzyme, 7 g of lactose and 3 g of magnesium stearte were each weighed and mixed uniformly. Then, 200 mg portions of this mixture were packed into No. 2 gelatin capsules and provided with an enteric coating to obtain enteric capsules.

EXAMPLE 5

Yolk lecithin, cholesterol and diacetyl phosphate were mixed in a molar ratio of 7:2:1, and 100 mg of the mixture was dissolved in 12.5 ml of chloroform. From this solution a thin film was formed on the wall of a flask. A dispersion was prepared by mixing this film with 25 ml of phosphate buffer solution containing 100 mg of the human leucocyte pepsin-like enzyme. After ultrasonic treatment, the dispersion was centrifuged at 110,000 g. The resulting precipitate was suspended in 3 ml of physiological saline solution and sterilized to obtain a human leucocyte pepsin-like enzyme-containing liposome inclusion preparation.

What is claimed is:

1. A human leucocyte enzyme having the following properties:
   (a) molecular weight of 35,000 to 41,000,
   (b) isoelectric point of pH 2.5 to 3.5,
   (c) maximum absorption at 278 nm,
   (d) positive ninhydrin reaction,
   (e) readily soluble in water and insoluble in ether and chloroform,
   (f) white powdery appearance,
   (g) anti-allergic and anti-immune complex disease activity, and
   (h) a high hydrolytic activity to hemoglobin in the acidic range, in substantially purified form.

2. A therapeutic composition for treating allergy and immune complex disease comprising a pharmaceutical carrier and an effective amount of the enzyme as set forth in claim 1.

3. A therapeutic composition as set forth in claim 2, wherein the composition is in a form selected from the group consisting of an injection preparation, an oral preparation, a suppository and an inhalant.

4. A therapeutic method for treating allergic disorders and immune complex diseases, comprising administering to a patient needing treatment for allergic disorders or immune complex diseases a therapeutically effective amount of a human leucocyte enzyme having the following properties:
   (a) molecular weight of 35,000 to 41,000,
   (b) isoelectric point of pH 2.5 to 3.5,
   (c) maximum absorption at 278 nm,
   (d) positive ninhydrin reaction,
   (e) readily soluble in water and insoluble in ether and chloroform,
   (f) white powdery appearance,
   (g) anti-allergic and anti-immune complex disease activity, and
   (h) a high hydrolytic activity to hemoglobin in the acidic range.

5. A therapeutic method as set forth in claim 4, comprising administering said human leucocyte enzume in a mixture with one or more pharmaceutically acceptable excipients and/or adjuvants.

6. A therapeutic method as set forth in claim 4, comprising administering said human leucocyte enzyme through one or more routes selected from the group consisting of injection, oral administration, rectal administration and inhalation.

7. A therapeutic method as set forth in claim 4, wherein said therapeutically effective amount is 1 to 1,000 mg per day.

8. A therapeutic method as set forth in claim 7, wherein said therapeutically effective amount is 50 to 500 mg per day.

9. A therapeutic method as set forth in claim 5, comprising administering said human leucocyte enzyme through one or more routes selected from the group consisting of injection, oral administration, rectal administration and inhalation.

10. A therepeutic method as set forth in claim 6, wherein said therapeutically effective amount is 1 to 1,000 mg per day.

11. A therapeutic method as set forth in claim 10, wherein said therapeutically effective amount is 50 to 500 mg per day.

* * * * *